United States Patent
Fischer et al.

[11] Patent Number: 5,453,516
[45] Date of Patent: Sep. 26, 1995

[54] PREPARATION OF 5-MEMBERED RING HETEROCYCLES

[75] Inventors: Rolf Fischer, Heidelberg; Rolf Pinkos, Bad Duerkheim, both of Germany

[73] Assignee: BASF Aktiengesellschaft, Ludwigshafen, Germany

[21] Appl. No.: 165,463

[22] Filed: Dec. 13, 1993

[30] Foreign Application Priority Data

Dec. 16, 1992 [DE] Germany .................. 42 42 451.8

[51] Int. Cl.$^6$ .............. C07D 207/27; C07D 207/26; C07D 307/28

[52] U.S. Cl. .............. 548/543; 548/517; 548/530; 548/539; 548/542; 548/544; 548/547; 548/551; 549/313; 549/322; 549/323; 549/324; 549/295; 549/326

[58] Field of Search ................ 548/543, 539, 548/530, 551; 549/326, 322, 313, 323, 295

[56] References Cited

U.S. PATENT DOCUMENTS

| | | | |
|---|---|---|---|
| 4,324,727 | 4/1982 | Merger et al. | 549/326 X |
| 4,831,166 | 5/1989 | Eckhardt et al. | 549/323 |
| 4,853,473 | 8/1989 | Fischer et al. | 549/326 |

FOREIGN PATENT DOCUMENTS 525506 2/1993 European Pat. Off. .

OTHER PUBLICATIONS

Chem. Abst., vol. 117, No. 17, Oct. 26, 1992, Abst. No. 170939q, Mitsuhiro et al.
J. Chem. Soc., Chem. Com. (1972) pp. 892–893, Posner et al.
J. Chem. Soc., Chem. Com. (1972) pp. 711–712, Herrmann et al.
J. Org. Chem. 31, (1966) 982–983, Gassman et al.
Pol. J. Chem. 60, (1986) 957–959, Bukowska et al.

*Primary Examiner*—Jacqueline Haley
*Attorney, Agent, or Firm*—Keil & Weinkauf

[57] ABSTRACT

A process for preparing 5-membered ring heterocycles of the general formula I

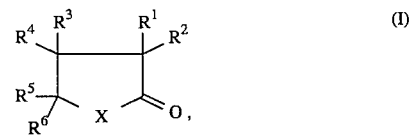

where
$R^1$ is methyl or hydroxyethyl,
$R^2, R^3, R^4, R^5$ and $R^6$ are hydrogen, $C_1$- to $C_{12}$-alkyl, $C_2$- to $C_{12}$-alkenyl, aryl, $C_3$- to $C_8$-cycloalkyl, $C_1$- to $C_{12}$-alkoxy, halogen, $C_2$- to $C_{20}$-alkoxycarbonylalkyl, $C_2$- to $C_{20}$-alkylcarbonyloxy, formyl, $C_2$- to $C_{20}$-formylalkyl, benzoyl or —CH(OR$^3$)(OR$^5$), or $R^3$ and $R^5$ together are a $C_2$- to $C_7$-alkylene chain which is unsubstituted or monosubstituted to pentasubstituted by $R^4$ or a =CH—CH=CH—CH= unit which is unsubstituted or monosubstituted to tetrasubstituted by $R^4$,
X is oxygen or N—$R^4$
by reacting 5-membered ring heterocycles of the general formula II

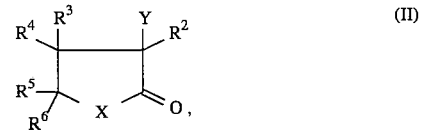

where $R^2$, $R^3$, $R^4$, $R^5$, $R^6$ and X have the abovementioned meanings and Y is hydrogen, acetyl or $C_2$- to $C_{20}$-alkoxycarbonyl, with dimethyl or ethylene carbonate in the presence of a nitrogen-containing base at from 50° to 300° C. and from 0.01 to 50 bar is described.

8 Claims, No Drawings

PREPARATION OF 5-MEMBERED RING HETEROCYCLES

The present application relates to a process for preparing 5-membered ring heterocycles by reacting corresponding 5-membered ring heterocycles carrying hydrogen in the alpha position to the carbonyl group with dimethyl or ethylene carbonate in the presence of nitrogen-containing bases as catalysts at elevated pressures.

J. Chem. Soc., Chem. Commun., (1972) pages 892 to 893 and J. Chem. Soc., Chem. Commun., (1973) pages 711 to 712 describe a process for preparing alpha-substituted lactones in yields of from 80 to over 90% by reacting gamma-butyrolactone and delta-valerolactone (−78° C.) with lithium diisopropylamide in tetrahydrofuran and subsequently alkylating with alkyl halides such as methyl iodide, ethyl iodide or allyl bromide (−40° C.).

It is furthermore known from J. Org. Chem., 31, (1966) 982 to 983 to react N-methylpyrrolidone with sodium amide in liquid ammonia and alkyl halides to give 1-methyl-3-alkylpyrrolidones.

It is common to the methods mentioned that alkyl halides and expensive lithium or sodium bases are employed and lithium or sodium halides are accordingly obtained as coupling products in stoichiometric amounts (salt production).

Pol. J. Chem. 60, (1986) 957 to 959 describes a process for preparing alpha-methoxycarbonylbutyrolactone by reacting butyrolactone with sodium hydride and dimethyl carbonate.

All these reactions cannot be carried out economically on the industrial scale, in particular because of the need to work at low temperatures or with highly reactive hydrides.

It is an object of the present invention to remedy the disadvantages previously mentioned.

We have found that this object is achieved by a novel and improved process for preparing 5-membered ring heterocycles of the general formula I

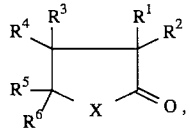

where $R^1$ is methyl or hydroxyethyl, $R^2, R^3, R^4, R^5$ and $R^6$ are hydrogen, $C_1$- to $C_{12}$-alkyl, $C_2$- to $C_{12}$-alkenyl, aryl, $C_3$- to $C_8$-cycloalkyl, $C_1$- to $C_{12}$-alkoxy, halogen, $C_2$- to $C_{20}$-alkoxycarbonylalkyl, $C_2$- to $C_{20}$-alkylcarbonyloxy, formyl, $C_2$- to $C_{20}$-formylalkyl, benzoyl or —CH($OR^{10}$)($OR^{11}$), or $R^3$ and $R^5$ together are a $C_2$- to $C_7$-alkylene chain which is unsubstituted or monosubstituted to pentasubstituted by $R^{12}$ or a =CH—CH=CH—CH= unit which is unsubstituted or monosubstituted to tetrasubstituted by $R^{12}$, X is oxygen or N—$R^{12}$ which comprises reacting 5-membered ring heterocycles of the general formula II

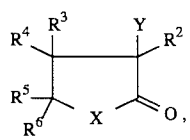

where $R^2$, $R^3$, $R^4$, $R^5$, $R^6$ and X have the abovementioned meanings and Y is hydrogen, acetyl or $C_2$- to $C_{20}$-alkoxycarbonyl, with dimethyl carbonate or ethylene carbonate in the presence of a nitrogen-containing base at from 50° to 300° C. and from 0.01 to 50 bar.

The process according to the invention can be carried out as follows:

The 5-membered ring heterocycles (lactones and lactams, especially butyrolactones and pyrrolidones) of the general formula II can be reacted with dimethyl carbonate or ethylene carbonate in the presence of nitrogen-containing bases, e.g. in pressure apparatuses at from 50° to 300° C., preferably 100° to 250° C., particularly preferably 150° to 230° C., and from 0.01 to 50 bar, preferably 0.5 to 5 bar, particularly preferably at the pressure which is established in the particular reaction mixture.

The reaction can be carried out batchwise or continuously in the gas phase, but preferably in the liquid phase.

It may be advantageous to carry out the reaction in the presence of gases which are inert under the reaction conditions, such as nitrogen or argon.

If lactams II in which the hydrogen atom of the NH group is unsubstituted are reacted with dimethyl carbonate or ethylene carbonate, depending on the reaction conditions partial or complete alkylation on the nitrogen also takes place in addition to alkylation in the 3-position.

The reaction of the lactones and lactams II in the liquid phase can be carried out, for example, by heating a mixture of II and if desired a solvent to the desired reaction temperature in the presence of dimethyl carbonate or ethylene carbonate and the nitrogen-containing bases. After reaction is complete, the reaction mixture can be cooled and fractionally distilled to obtain the desired lactones or lactams I.

The reaction according to the invention can be carried out in the absence of solvents. However, it may be advantageous to work in the presence of solvents. Solvents which can be used are, for example, acyclic or cyclic ethers such as diethyl ether, tetrahydrofuran and dioxane, aromatics such as benzene, toluene and the xylenes, and chlorinated hydrocarbons such as chloroform and methylene chloride.

The amount of solvent, based on the lactones and lactams II employed, is from 0 to 90% by weight, preferably 5 to 80% by weight, particularly preferably 20 to 60% by weight.

The molar ratio of lactones and lactams II to dimethyl carbonate or ethylene carbonate is as a rule 10:1–1:1, preferably 5:1–2:1. It is possible to work in excess dimethyl carbonate or ethylene carbonate as a solvent.

Suitable nitrogen-containing bases are ammonia, primary, secondary and tertiary amines such as those of the general formula III having aliphatic, cycloaliphatic, heteroaromatic and/or araliphatic substituents. At the same time, two aliphatic substituents can also be closed to form a ring. Diamines are also suitable.

Examples of these bases are:

ammonia, methylamine, ethylamine, hexylamine and cyclohexylamine, dimethylamine, diethylamine, dibutylamine and dicyclohexylamine, trimethylamine, dimethylethylamine, triethylamine, tri-n-propylamine, triisopropylamine, tributylamine, trioctylamine, tricyclohexylamine, trihexadecylamine, tricyclohexylamine, diphenylmethylamine, dimethylbenzylamine, dibenzylmethylamine, tribenzylamine, N,N-tetramethylhexamethylenediamine, hexamethylenediamine and tetramethylenediamine, 4-dimethylaminopyridine, urotropine, piperidine, N-methylpiperidine, pyrrolidine, N-methylpyrrolidine, hexamethylenimine, N-ethylhexamethylenimine, N-methylimidazole, 1,4-diazabicyclo[4.3.0]octane (DABCO), morpholine, piperazine and pyrrolidine.

Furthermore, amidines such as 1,5-diazabicyclo[4.3.0]non-5-ene (DBN), 1,8-diazabicyclo[5.4.0]undec-7-ene (DBU) and guanidine are suitable.

The tertiary amines are preferred, particularly preferably $C_1$- to $C_8$-trialkylamines.

The molar ratio of lactones and lactams II to the nitrogen-containing bases is as a rule 100:1–1:1, preferably 20:1–3:1.

The butyrolactones and pyrrolidones of the general formula II used as starting compounds are generally accessible compounds which can be prepared, for example, according to Houben-Weyl, Methoden der Organischen Chemie (Methods of organic chemistry), 4th Edition, Volume VI/2, pages 571 to 759.

Suitable butyrolactones and pyrrolidones of the general formula II are e.g. gamma-butyrolactone, pyrrolidone, N-methylpyrrolidone, 4-methylbutyrolactone, 4,4-dimethyl-gamma-butyrolactone, 2,3-dimethylbutyrolactone, 3,4-dimethylbutyrolactone, 2-(hydroxyethyl)butyrolactone, 4-methyl-2-(hydroxyethyl)butyrolactone, 4-chlorobutyrolactone, 3-methoxybutyrolactone, 3,5-dimethylpyrrolidone, N-vinylpyrrolidone, N-cyclohexylpyrrolidone, N-octylpyrrolidone, 3-vinylbutyrolactone, 4-formylbutyrolactone, 4-methoxycarbonylbutyrolactone, 3-acetylbutyrolactone, 4-vinylbutyrolactone, 2-methoxycarbonylbutyrolactone and 2-acetylbutyrolactone.

The substituents $R^1$, $R^2$, $R^3$, $R^4$, $R^5$, $R^6$, $R^7$, $R^8$, $R^9$, X and Y in the compounds I, II and III have the following meanings:

$R^1$ is
  methyl or
  hydroxyethyl, $R^2$, $R^3$, $R^4$, $R^5$, $R^6$, $R^7$, $R^8$ and $R^9$ are
  hydrogen,
  $C_3$- to $C_8$-cycloalkyl such as cyclopropyl, cyclobutyl, cyclopentyl, cyclohexyl, cycloheptyl and cyclooctyl, preferably $C_4$- to $C_8$-cycloalkyl such as cyclobutyl, cyclopentyl, cyclohexyl, cycloheptyl and cyclooctyl, particularly preferably $C_5$- to $C_8$-cycloalkyl such as cyclopentyl, cyclohexyl and cyclooctyl, $R^2$, $R^3$, $R^4$, $R^5$ and $R^6$ are
  $C_1$- to $C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, preferably $C_1$- to $C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$- to $C_4$-alkyl such as methyl, ethyl, n-propyl, isopropyl, n-butyl, isobutyl, sec-butyl and tert-butyl,
  $C_2$- to $C_{12}$-alkenyl, preferably $C_2$- to $C_8$-alkenyl such as vinyl, allyl, but-2-en-1-yl, but-4-en-1-yl, but-4-en-2-yl, pent-2-en-1-yl and 2,2-dimethylpent-1-en-1-yl, particularly preferably $C_2$- to $C_8$-alkenyl such as vinyl, allyl, but-2-en-1-yl and but-4-en-2-yl,
  $C_1$- to $C_{12}$-alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, n-nonoxy, isononoxy, n-decoxy, isodecoxy, n-undecoxy, isoundecoxy, n-dodecoxy and isododecoxy, preferably $C_1$- to $C_8$-alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy and isooctoxy, particularly preferably $C_1$- to $C_4$-alkoxy such as methoxy, ethoxy, n-propoxy, isopropoxy, n-butoxy, isobutoxy, sec-butoxy and tert-butoxy,
  halogen such as fluorine, chlorine, bromine and iodine, preferably fluorine, chlorine and bromine, particularly preferably fluorine and chlorine,
  $C_2$- to $C_{20}$-alkoxycarbonylalkyl, preferably $C_2$- to $C_8$-alkoxycarbonylalkyl such as methoxycarbonylmethyl, methoxycarbonylethyl, ethoxycarbonylmethyl and ethoxycarbonylethyl, particularly preferably methoxycarbonylmethyl,
  $C_2$- to $C_{20}$-alkylcarbonyloxy, preferably $C_2$- to $C_8$-alkylcarbonyloxy such as methylcarbonyloxy, ethylcarbonyloxy, n-propylcarbonyloxy and isopropyl carbonyloxy, particularly preferably methoxycarbonyloxy,
  aryl such as phenyl, 1-naphthyl, 2-naphthyl, 1-anthryl, 2-anthryl and 9-anthryl, preferably phenyl, 1-naphthyl and 2-naphthyl, particularly preferably phenyl,
  formyl,
  $C_2$- to $C_{20}$-formylalkyl, preferably $C_2$- to $C_8$-formylalkyl such as formylmethyl and formylethyl, particularly preferably formylmethyl,
  benzoyl,
  —CH(OR$^3$)(OR$^5$), $R^7$, $R^8$ and $R^9$ are
  $C_1$- to $C_{30}$-alkyl such methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, preferably $C_1$- to $C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$- to $C_4$-alkyl such as methyl, ethyl, n-propyl, isopropyl, n-butyl, isobutyl, sec-butyl and tert-butyl,
  $C_7$- to $C_{20}$-aralkyl, preferably $C_7$- to $C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ and $R^5$ or $R^7$ and $R^8$ are
  jointly
  a $C_2$- to $C_7$-alkylene chain such as —(CH$_2$)$_2$—, —(CH$_2$)$_3$—, —(CH$_2$)$_4$—, —(CH$_2$)$_5$—, —(CH$_2$)$_6$— and —(CH$_2$)$_7$—, preferably —(CH$_2$)$_3$— and —(CH$_2$)$_4$—, particularly preferably —(CH$_2$)$_4$—,
  a $C_2$- to $C_7$-alkylene chain which is substituted by 1 to 5 identical or different $R^4$ radicals, preferably $C_3$- and $C_4$-alkylene, particularly preferably $C_4$-alkylene, $R^3$ and $R^5$ are
  =CH—CH=CH—CH=, a =CH—CH=CH—CH= unit substituted by 1 to 5 identical or different $R^9$ radicals, preferably a =CH—CH=CH—CH= unit substituted by an identical or different $R^4$ radical, X is
  oxygen or
  N—$R^9$,
Y is
  hydrogen,
  acetyl,
  $C_2$- to $C_{20}$-alkoxycarbonyl, preferably $C_2$- to $C_8$-alkoxycarbonyl, particularly preferably $C_2$- to $C_4$-alkoxycarbonyl such as methoxycarbonyl, ethoxycarbonyl, n-propoxycarbonyl and isopropoxycarbonyl.

EXAMPLES

Example 1

A mixture of 25 g (250 mmol) of 4-methylbutyrolactone, 112.5 g of dimethyl carbonate and 3 g (50 mmol) of trimethylamine was heated to 200° C. in an autoclave and stirred at this temperature for 5 hours. After cooling, 18.6 g (74%) of 2,4-dimethylbutyrolactone; b.p.: 70°–74° C./10 mbar (selectivity 83%), and 2.3 g of unreacted gamma-butyrolactone were obtained by fractional distillation.

Example 2

A mixture of 21.5 g (250 mmol) of gamma-butyrolactone, 45 g (500 mmol) of dimethyl carbonate and 0.93 g (12.5 mmol) of dimethylethylamine was heated to 200° C. in an autoclave and stirred at this temperature for 5 hours. After cooling, 13.3 g (53%) of 2-methylbutyrolactone (selectivity 74%) and 6 g of unreacted gamma-butyrolactone were obtained by quantitative gas-chromatographic analysis of the discharged reaction mixture.

Examples 3 to 14

Mixtures of 21.5 g of gamma-butyrolactone, 112.5 g of dimethyl carbonate and 5 mol % (based on gamma-butyrolactone employed) of various nitrogen bases were stirred at 200° C. for 5 hours in autoclaves. Table 1 contains the amounts of 2-methylbutyrolactone analyzed by gas chromatography.

Example 15

A mixture of 25.3 g of N-methylpyrrolidone, 115 g of dimethyl carbonate and 3.7 g of ethyldimethylamine was heated to 200° C. in the course of an hour in an autoclave and stirred at this temperature for 5 hours. Quantitative gas-chromatographic analysis showed that the mixture discharged from the reaction contained 27 mol % of 2,5-dimethylpyrrolidone (based on N-methylpyrrolidone employed) in addition to 61 mol % of unreacted N-methylpyrrolidone. The 2,5-dimethylpyrrolidone yield is therefore 27% and the selectivity 69%.

Example 16

A mixture of 25.6 g of 2-acetylbutyrolactone, 45 g of dimethyl carbonate and 3 g of ethyldimethylamine was heated to 200° C. in the course of an hour and stirred at this temperature for 5 hours. After cooling, 12.9 g of 2-methylbutyrolactone (65%, based on 2-acetylbutyrolactone employed) were obtained by fractional distillation.

Example 17

A mixture of 26.7 g of 2-methoxycarbonylbutyrolactone, 40.5 g of dimethyl carbonate and 0.7 g of ethyldimethylamine was reacted and worked up as described in Example 16. In this way, 12.3 g of 2-methylbutyrolactone (66%, based on 2-methoxycarbonylbutyrolactone employed) were obtained.

We claim:

1. A process for preparing 5-membered ring heterocycles of the formula I

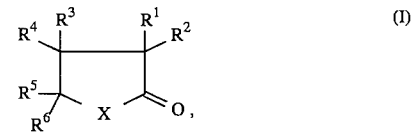

where
  $R^1$ is methyl or hydroxyethyl, $R^2$, $R^3$, $R^4$, $R^5$ and $R^6$ are hydrogen, $C_1$- to $C_{12}$-alkyl, $C_2$- to $C_{12}$-alkenyl, aryl, $C_3$- to $C_8$-cycloalkyl, $C_1$- to $C_{12}$-alkoxy, halogen, $C_2$- to $C_{20}$-alkoxycarbonylalkyl, $C_2$- to $C_{20}$-alkylcarbonyloxy, formyl, $C_2$- to $C_{20}$-formylalkyl, benzoyl or

TABLE

Preparation of 2-methylbutyrolactone using various nitrogen bases

| Example No. | N base | 2-Methylbutyrolactone [mol %] | Gamma-butyrolactone [mol %] | 2-Methylbutyrolactone selectivity [%] |
| --- | --- | --- | --- | --- |
| 4 | trimethylamine | 63 | 16 | 75 |
| 5 | triethylamine | 57 | 20 | 71 |
| 6 | dibutylamine | 69 | 10 | 77 |
| 7 | piperidine | 53 | 23 | 69 |
| 8 | DBN | 51 | 22 | 65 |
| 9 | DBU | 38 | 32 | 56 |
| 10 | DABCO | 46 | 23 | 60 |
| 11 | 4-dimethylaminopyridine | 29 | 36 | 45 |
| 12 | tributylamine | 58 | 19 | 72 |
| 13 | ammonia | 22 | 52 | 46 |
| 14 | n-pentylamine | 28 | 39 | 46 |

—CH($OR^{10}$)($OR^{11}$) wherein
  $R^{10}$, $R^{11}$ and $R^{12}$ are hydrogen, $C_1$–$C_{30}$-alkyl, $C_3$–$C_8$-cycloalkyl, or $C_7$–$C_{20}$-aralkyl, or wherein $R^{10}$ and $R^{11}$ together are a $C_2$- to $C_7$-alkylene chain which is unsubstituted or monosubstituted to pentasubstituted by $R^{12}$, or a =CH—CH— CH—CH= unit which is unsubstituted or monosubstituted to tetrasubstituted by $R^{12}$, X is oxygen or N—$R^{12}$ which comprises reacting 5-membered ring heterocycles of the formula II

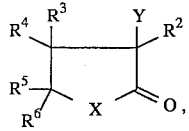
(II)

where $R^2$, $R^3$, $R^4$, $R^5$, $R^6$ and X have the abovementioned meanings and Y is hydrogen, acetyl or $C_2$- to $C_{20}$-alkoxycarbonyl, with dimethyl carbonate or ethylene carbonate in the presence of a nitrogen-containing base at from 50° to 300° C. and from 0.01 to 50 bar.

2. A process for preparing 5-membered ring heterocycles of the general formula I as claimed in claim 1, wherein $R^2$ is hydrogen.

3. A process for preparing 5-membered ring heterocycles of the general formula I as claimed in claim 1, wherein the nitrogen-containing base employed is ammonia, primary, secondary or tertiary amines or amidines.

4. A process for preparing 5-membered ring heterocycles of the general formula I as claimed in claim 1, wherein the 5-membered ring heterocycles of the general formula II are kept in a molar ratio of 10:1–1:1 to the dimethyl carbonate or ethylene carbonate.

5. A process for preparing 5-membered ring heterocycles of the general formula I as claimed in claim 1, wherein the nitrogen-containing base is of the general formula III

(III)

where
  $R^7$, $R^8$ and $R^9$ are hydrogen, $C_1$- to $C_{30}$-alkyl, $C_3$- to $C_8$-cycloalkyl or $C_7$- to $C_{20}$-aralkyl, or $R^7$ and $R^8$ form a $C_2$- to $C_7$-alkylene chain which is unstubstituted or monosubstituted to pentasubstituted by $R^{12}$.

6. A process for preparing 5-membered ring heterocycles of the general formula I as claimed in claim 1, wherein the nitrogen-containing base employed is 1,5-diazabicyclo[4.3.0]non-5-ene (DBN) or 1,8-diazabicyclo[5.4.0]undec-7-ene (DBU).

7. A process for preparing 5-membered ring heterocycles of the general formula I as claimed in claim 1, wherein the 5-membered ring heterocycles of the general formula II are employed in a molar ratio of 100:1–1:1 to the nitrogen-containing base.

8. A process for preparing 5-membered ring heterocycles of the general formula I as claimed in claim 1, wherein the reaction is carried out at temperatures from 100° to 250° C.

* * * * *